United States Patent [19]

Mitchiner

[11] Patent Number: 5,168,875
[45] Date of Patent: Dec. 8, 1992

[54] ELONGATED STRIP ELECTRODE ARRANGEMENT AND METHOD

[75] Inventor: Robert K. Mitchiner, Longmont, Colo.

[73] Assignee: Staodyn, Inc., Longmont, Colo.

[21] Appl. No.: 684,001

[22] Filed: Apr. 11, 1991

[51] Int. Cl.⁵ ............................ A61B 5/04; A61N 1/04
[52] U.S. Cl. ............................ 128/640; 128/798; 128/802
[58] Field of Search ............................ 128/639–641, 128/644, 783, 798, 802, 803; 606/32

[56] References Cited

U.S. PATENT DOCUMENTS

| | | | |
|---|---|---|---|
| 2,943,628 | 7/1960 | Howell | 128/640 |
| 3,565,059 | 2/1971 | Hauser et al. | 128/640 |
| 4,094,309 | 6/1978 | Grzenia | 128/644 |
| 4,243,051 | 1/1981 | Wittemann . | |
| 4,243,052 | 1/1981 | Bailey | 128/798 |
| 4,248,247 | 2/1981 | Ware et al. . | |
| 4,265,253 | 5/1981 | Abraham | 128/798 |
| 4,633,879 | 1/1987 | Ong . | |
| 4,657,023 | 4/1987 | Kuhn . | |
| 4,736,752 | 4/1988 | Munck et al. | 128/798 |
| 4,771,783 | 9/1988 | Roberts . | |
| 4,838,273 | 6/1989 | Cartmell | 128/640 |
| 4,919,148 | 4/1990 | Muccio . | |
| 4,955,381 | 9/1990 | Way et al. . | |

FOREIGN PATENT DOCUMENTS

| | | | |
|---|---|---|---|
| 0097436 | 1/1984 | European Pat. Off. | 128/798 |
| 2292490 | 6/1976 | France | 128/798 |

*Primary Examiner*—Lee S. Cohen
*Attorney, Agent, or Firm*—Robert E. Harris

[57] ABSTRACT

An elongated strip electrode arrangement and method are disclosed. The electrode includes an electrically conductive layer having a layer of conductive adhesive at one side and an electrically non-conductive layer at the other side with the non-conductive layer having a series of longitudinally spaced pairs of apertures therein through which a connector pin is insertable to establish and maintain electrical contact between the pin and the conductive layer. The apertures of each aperture pair are closely spaced from one another so that a connector pin when inserted through one of the apertures a sufficient distance can extend from the electrode through the other aperture. The longitudinally extending series of aperture pairs enables selection of electrode strips of different lengths from a roll of the strip electrode. The strip electrode includes an elongated non-conductive strip of small width aligned with the series of aperture pins and positioned between the conductive layer and the adhesive layer to provide user protection, and a piece of adhesive can also be utilized to further prevent retraction of a pin when positioned in an aperture pair.

16 Claims, 2 Drawing Sheets

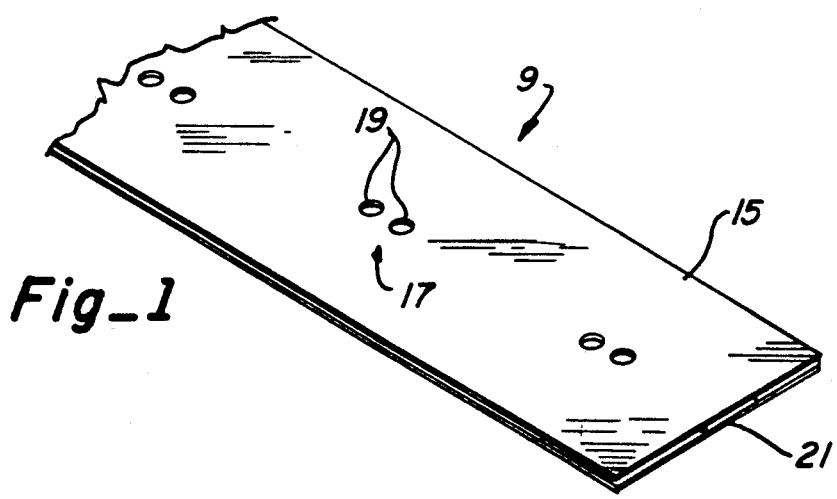
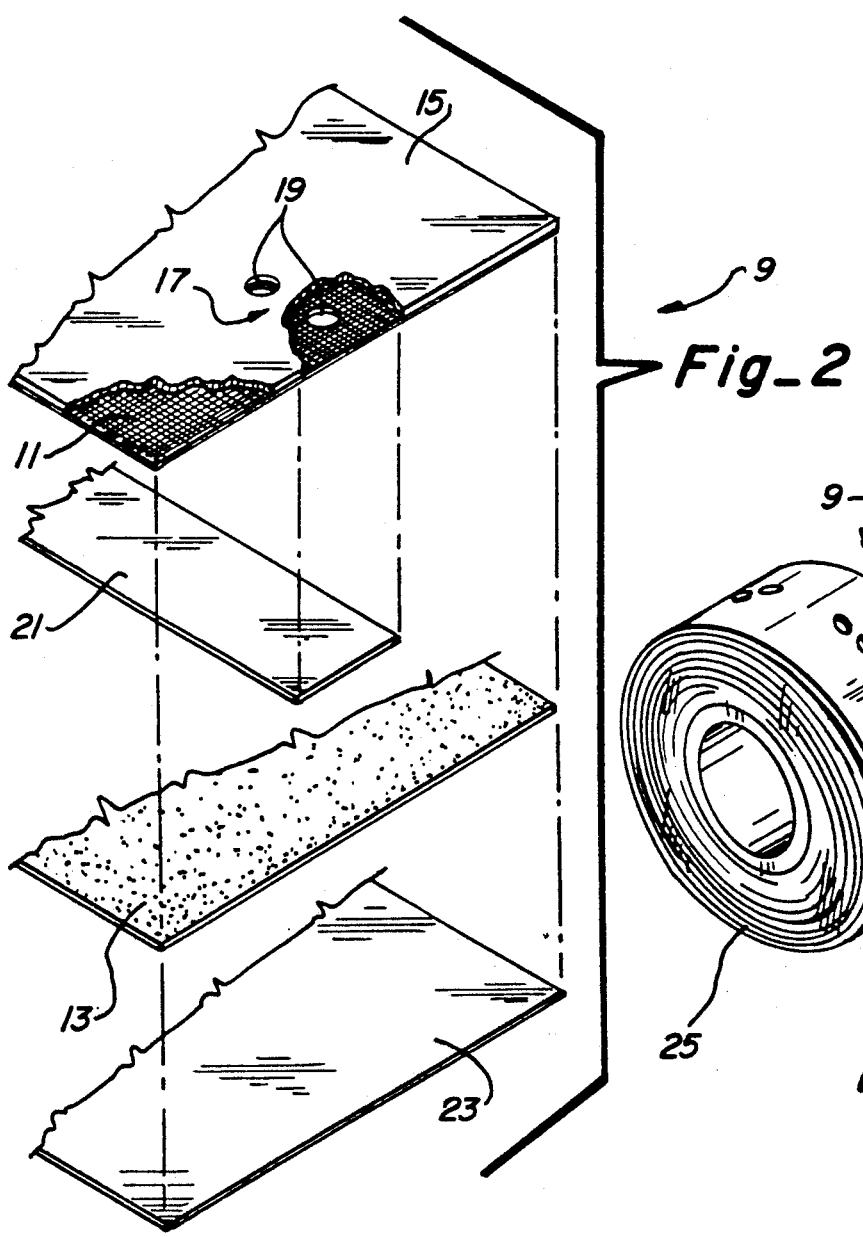
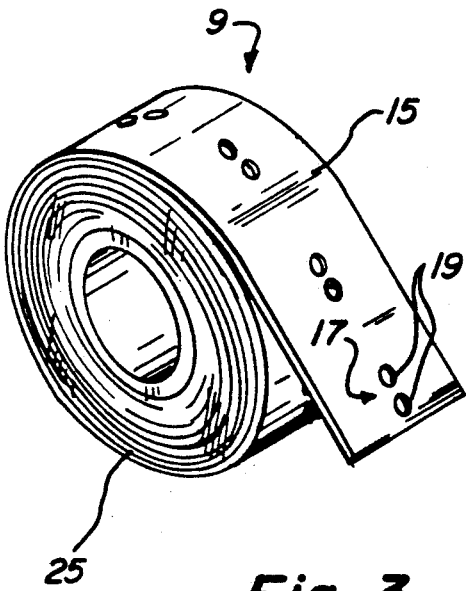

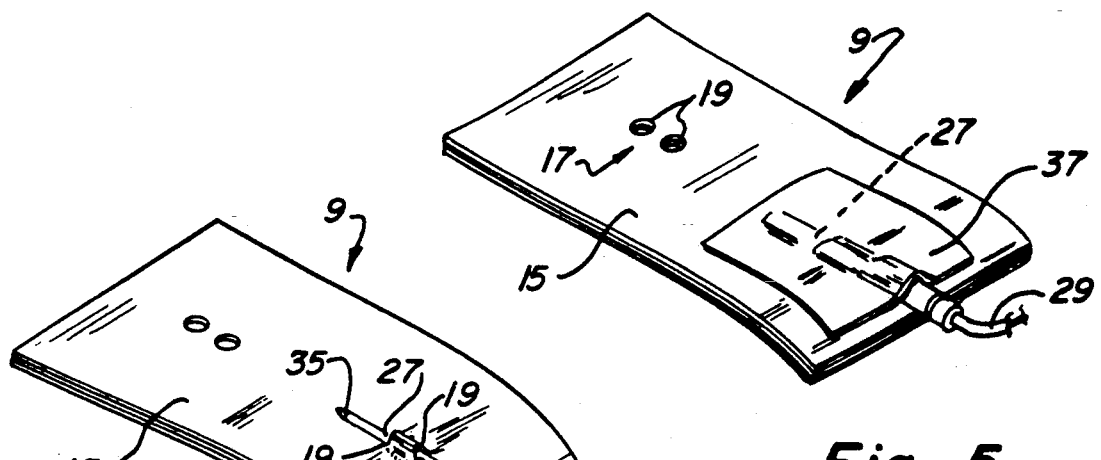
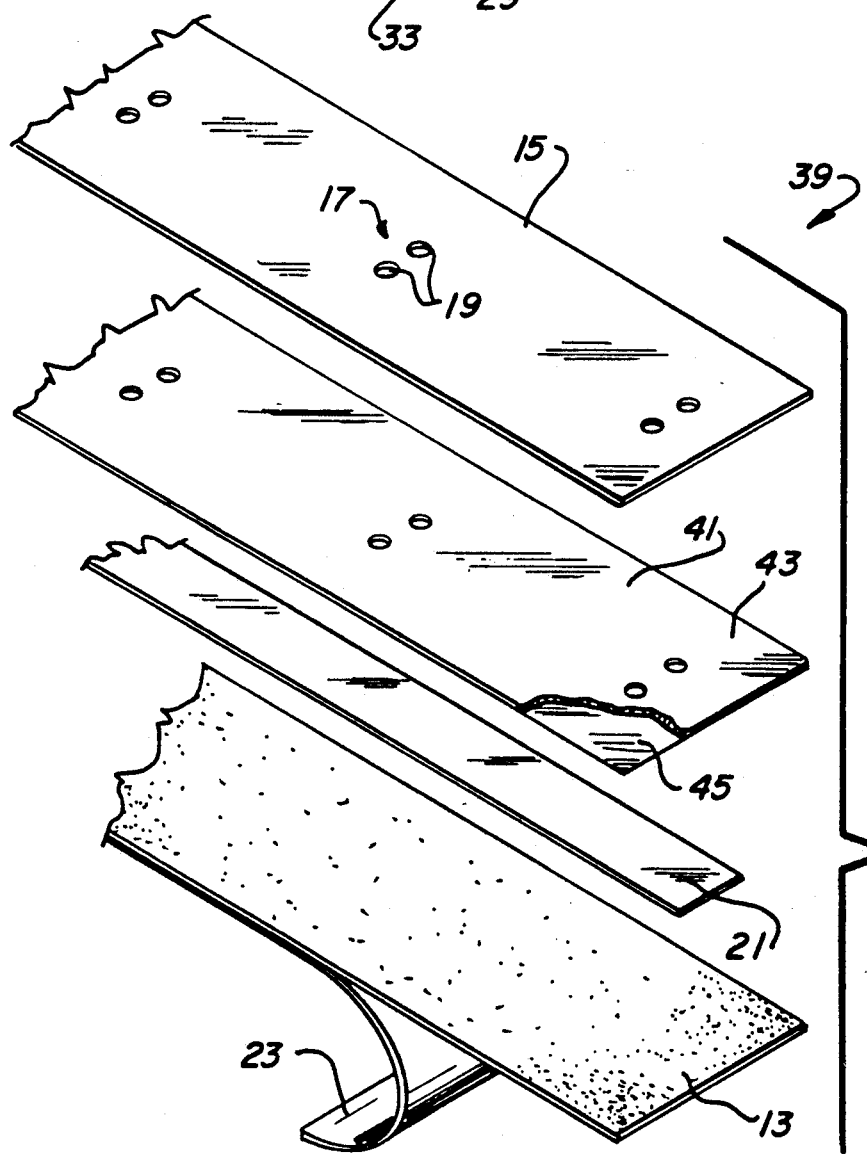

ELONGATED STRIP ELECTRODE ARRANGEMENT AND METHOD

FIELD OF THE INVENTION

This invention relates to an electrode arrangement and method, and, more particularly, relates to an elongated medical electrode strip arrangement and method.

BACKGROUND OF THE INVENTION

Electrode arrangements and methods are now quite widely utilized in connection with medical apparatus to apply electrical signals through electrodes to the skin of a user, as well as to monitor and/or sense electrical signals at the skin of a user.

Electrodes are widely known, for example, that are usable in connection with transcutaneous nerve stimulating (TENS) units to apply electrical signals to a user with the applied electrical signals being suitable for stimulating nerve fibers to thereby suppress pain, and such electrodes, again by way of example, are known to be useful in connection with monitoring apparatus (such as heart monitoring) by detecting electrical signals at the skin of a user.

In the prior art, U.S. Pat. No. 4,771,783 (Roberts) shows a biomedical electrode having an electrically conductive metal film with a conductive adhesive at one side and an insulative web at the other side and with a conductor plate inserted from the edge of the electrode to make contact with the electrically conductive film. U.S. Pat. No. 4,248,247 (Ware et al.) shows a post-operative electrode having a conductive sheet of carbon loaded rubber with a conductive adhesive at one side and a foam plastic backing layer at the other side and with a wire lead extending from the edge of the electrode along the length of the conductive rubber sheet to make contact with the conductive rubber sheet.

U.S. Pat. No. 4,243,051 (Wittemann) shows a disposable electrode having a conductive mesh layer with a conductive adhesive material at one side and a fabric layer at the other side and also shows a wire having insulating tape thereover extending from the edge of the electrode across the conductive mesh layer. U.S. Pat. No. 4,736,752 (Munck et al.) shows a transcutaneous medical electrode having a conductive ink pattern as the conductive layer with an adhesive conductor at one side and a backing sheet upon which the conductive ink pattern is deposited at the other side.

U.S. Pat. No. 4,657,023 (Kuhn) shows a self-adhering electrode having a metal conductive layer with a temperature sensitive adhesive tape at one side and a conductive substrate at the other side, with a removable liner being deposited over the conductive substrate, and with the adhesive tape having an aperture in the center thereof for allowing a tab on the metal conductive layer to extend upwardly from the top of the electrode. U.S. Pat. No. 4,955,381 (Way et al.) shows a multipad-multifunction electrode having a metal foil contactable with the ends of a connector lead through apertures in the plastic foam backing cover. U.S. Pat. No. 4,633,879 (Ong) shows an electrode with a disposable interface member with the electrode having an electrically conductive and adhesive sheet with an insulative backing and a snap connector extending through the backing sheet to make contact with the electrically conductive and adhesive sheet.

While some known electrodes have been achieved that are relatively simple in structure, there still exists a need for an electrode with a structure allowing the electrode to be of sufficiently low cost to be truly disposable and yet be effective for a particular short use, such as, for example, as a diagnostic electrode capable of determining usability of a particular device with respect to a particular user (such as, for example, use of a TENS unit to demonstrate that the unit is effective with respect to suppressing pain of that user).

SUMMARY OF THE INVENTION

This invention provides an improved electrode arrangement and method. An elongated strip electrode is realized having an electrically conductive layer between an electrically conductive adhesive layer and an electrically non-conductive layer with the non-conductive layer having aperture means to receive a relatively non-flexible connector.

The aperture means preferably includes a pair of apertures that are closely spaced with respect to one another so that a pin when inserted a sufficient distance in one aperture extends from the electrode through the other aperture to thereby maintain the side of the pin in good electrical contact with the conductive layer of the electrode. The elongated strip may be provided in a roll, and a series of aperture pairs are preferably longitudinally spaced along the elongated strip to enable selection of electrodes of varying lengths. The electrode also preferably includes a strip of relatively narrow width (with respect to the width of the conductive layer) aligned with the aperture pairs and positioned between the conductive layer and the adhesive layer to protect the user, and a small adhesive piece can also be used over the apertures to contact a pin positioned therein to better maintain the pin within the apertures.

It is therefore an object of this invention to provide an improved electrode arrangement and method.

It is another object of this invention to provide an improved electrode arrangement and method for providing a strip electrode.

It is still another object of this invention to provide an improved electrode arrangement and method utilizing an electrically conductive layer having an electrically non-conductive layer contiguous thereto, with the non-conductive layer having aperture means therein capable of receiving a relatively non-flexible end portion of a connector.

It is still another object of this invention to provide an improved electrode arrangement and method that utilizes an electrically non-conductive layer with a pair of closely spaced apertures to receive a connector pin so that the side of the pin is maintained in electrical contact with an electrical conductive layer adjacent to the non-conductive layer.

It is still another object of this invention to provide an improved electrode arrangement and method that utilizes an electrically non-conductive layer with a pair of closely spaced apertures to receive a connector pin as well as adhesive means to facilitate maintaining the connector pin in said apertures.

It is still another object of this invention to provide an improved electrode arrangement and method that utilizes an electrically non-conductive layer with a series of aperture pairs to enable selection of varying lengths of electrode.

It is still another object of this invention to provide an improved electrode arrangement and method that utilizes an electrode strip formed into a roll.

It is still another object of this invention to provide an improved electrode arrangement and method that utilizes a relatively narrow width non-conductive strip positioned between the conductive layer of an electrode and aligned with a series of apertures in a non-conductive layer.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate complete embodiments of the invention according to the best mode so far devised for the practical application of the principles thereof, and in which:

FIG. 1 is a perspective view of the electrode of this invention;

FIG. 2 is a exploded view of the electrode shown in FIG. 1;

FIG. 3 is a perspective view of a strip electrode as shown in FIGS. 1 and 2 with the strip electrode formed into a roll;

FIG. 4 is a perspective view of the strip electrode with a connector pin inserted;

FIG. 5 is a perspective view of the electrode with the connector pin inserted and with an adhesive piece thereover; and FIG. 6 is an exploded view illustrating an alternate embodiment of the electrode.

DESCRIPTION OF THE INVENTION

The now preferred embodiment of electrode 9 of this invention is best shown in FIGS. 1 and 2. As shown, electrode 9 is a longitudinally elongated strip electrode that includes an electrically conductive layer 11. An electrically conductive adhesive layer 13 is positioned contiguous to one side of conductive layer 11 and an electrically non-conductive layer 15 is positioned contiguous to the other side of conductive layer 11.

Electrically conductive layer 11 is preferably a conductive ink (such as a metalized ink) that is deposited, as by printing, on the inner side of non-conductive insulating layer 15. Ink layer 11 can be solid or can be deposited in a particular pattern, such as, for example, in a mesh-like configuration.

Conductive adhesive layer 13 can be formed of a conventional electrically conductive material now normally utilized for medical electrodes, and non-conductive layer 15 can likewise be formed of conventional non-conductive material, such as, for example, paper or vinyl, now normally utilized for medical electrodes.

As shown in FIGS. 1 and 2, non-conductive layer 15 has at least one pair 17 of closely spaced apertures 19 therein. With conductive layer 11 painted on the inward side of non-conductive layer 15, apertures 19 also extend through the conductive ink layer. A non-conductive protective strip 21 (which strip may, for example, be of the same material as non-conductive layer 15) of narrow width (relative to the width of the conductive layer) is aligned with apertures 19 and is positioned between conductive layer 11 and adhesive layer 13 to provide protection to a user by promoting current dispersion throughout the electrode.

A removable release liner 23 of conventional material (such as polyethylene, for example) is also normally positioned over the outer side of the adhesive layer to protect the adhesive layer until use of the electrode.

As indicated in FIG. 1, strip electrode 9 can include a series of aperture pairs 17 spaced longitudinally along the elongated electrode. This allows the electrode to be longitudinally sized, as desired, by simply severing a length of the electrode from the remainder thereof, so long as the severed electrode includes at least one aperture pair 17 to enable connection of the electrode to the electrical device to be utilized.

As indicated in FIG. 3, strip electrode 9 may be a continuous strip formed into a roll 25 with the strip being unrolled as needed to provide each strip electrode.

Electrical connection to electrode 9 is effected by use of a connector pin 27 (or other relatively non-flexible connector). The connector is normally metallic and is electrically a part of, or connected with, lead 29 to connect the electrode to the electrical apparatus to be utilized, such as, for example, a TENS unit.

Connector pin 27, as indicated in FIG. 4, has a side portion 31 which extends from connecting junction 33 to end 35 of the pin with side portion 31 being longer than the spacing between apertures 19 of each aperture pair 17 in non-conductive layer 15. This enables connector pin 27 to be inserted into one aperture and then, when inserted a sufficient distance, end 35 of the pin can be directed outwardly through the other aperture of the aperture pair (as indicated in FIG. 4). The use of dual apertures has been found to better maintain the pin in position with side 31 of the pin in good electrical engagement with conductive layer 11 of the electrode. When so positioned, the pin resists withdrawal from the dual apertures to a much greater degree than does withdrawal of a pin extending through only a single aperture.

As indicated in FIG. 5, a still greater degree of pin maintenance can be effected utilizing dual apertures and by also providing a small piece 37 of adhesive (such as adhesive tape, for example) over the outward side of non-conductive layer 15 after the pin is inserted through the dual apertures 19.

An alternate embodiment 39 of the electrode of this invention is shown in FIG. 6. As shown, electrically conductive layer 41 is formed of a carbon loaded material 43 (such as carbon loaded rubber, for example) having a metalized side 45 (i.e., having a metal such as silver deposited on the side adjacent to the adhesive layer).

While not shown, it is to be realized that other modifications of the electrode might also be utilized without departing from the intended invention. For example, in some uses, a thin metal sheet could be used as the electrically conductive layer, and/or diverse insulating materials could be used for insulating layer 11 and/or protective strip 21. In all cases, however, the strip electrode is made of readily flexible materials.

For use, a section of the electrode strip is unrolled from a roll (if the strip electrode has been formed into a roll) and severed from the roll to the desired length. The conductor pin is then inserted through dual apertures 19 (and covered with an adhesive piece, if utilized), and the release liner is removed from the adhesive side of the electrode. The electrode is then placed on the skin of a user and the connector lead connected with an electrical apparatus to be utilized (while not shown, a return electrode is also normally placed on the skin of a user and likewise connected through a connector lead to the apparatus to be used). The apparatus is then ready for use.

The electrode of this invention is intended primarily for short term use and thereafter discarded. Since the strip electrode is quite inexpensive, it is particularly well suited to be used as a disposable electrode, and is also particularly well suited to perform an intended short term function such as, for example, being used for diagnostic purposes to determine effective use of an apparatus (such as a TENS unit, for example) in accomplishing its intended purpose (such as, for example, in the case of a TENS unit to demonstrate suppression of pain with respect to a particular user).

In view of the foregoing, it is to be appreciated that this invention provides an improved electrode arrangement and method.

What is claimed is:

1. A disposable diagnostic electrode usable in conjunction with electrical connecting means having an end portion and an elongated side portion that terminates at said end portion, said electrode comprising:
   an electrically conductive layer;
   an electrically conductive adhesive layer one side of which is positioned contiguous to one side of said conductive layer and the other side of which is adapted to engage the skin of a user; and
   an electrically non-conductive insulating layer one side of which is positioned contiguous to the side of said conductive layer opposite to that of said one side, said insulating layer having a series of spaced aperture means therein with each of said aperture means being capable of separately receiving said end portion of said electrical connecting means with said insulating layer being flexible relative to said elongated side portion of said electrical connecting means whereby, when said end portion of said connecting means is inserted through said aperture means of said insulating layer, at least a part of said elongated side portion is in engagement with said conductive layer to establish an electrical connection thereat.

2. The electrode of claim 1 wherein said conductive layer is conductive ink deposited on said insulating layer.

3. The electrode of claim 1 wherein said conductive layer is a carbon-loaded material with said one side being metalized.

4. The electrode of claim 1 wherein each of said series of aperture means in said insulating layer includes a pair of apertures spaced a distance from one another less than said elongated side portion of said electrical connecting means usable with said electrode whereby said end portion may be inserted inwardly through one of said apertures a distance sufficient to cause said end portion to extend outwardly through the other of said apertures.

5. The electrode of claim 4 wherein said electrode has adhesive means engaging the side of said insulating layer opposite to that of said one side contiguous to said conductive layer with said adhesive means engaging said end portion of said electrical connecting means outwardly of said apertures.

6. The electrode of claim 1 wherein said electrode has an electrically non-conductive removable liner contiguous to said other side of said adhesive layer.

7. A disposable diagnostic electrode arrangement, comprising:
   an electrode having an electrically conductive layer with an electrically conductive adhesive layer at one side and an electrically non-conductive layer at the other side, said non-conductive layer having a series of spaced pairs of apertures therein with the apertures of each said pair being closely spaced with respect to one another; and
   an electrical pin connector having a side portion and an end portion, the length of said side portion being greater than the distance between the apertures of each said pair of apertures in said non-conductive layer whereby each said pair of apertures is capable of receiving said electrical pin connector so that said electrical pin connector, when inserted through one of said apertures of a said pair of spaced apertures a sufficient distance, has the end portion extending from the other of said apertures of the said pair of apertures so that the side portion of said electrical pin connector is maintained in electrical engagement with said electrically conductive layer of said electrode.

8. The arrangement of claim 7 wherein said arrangement includes an adhesive means adjacent to said apertures and engaging said electrical pin connector when positioned through said apertures.

9. The arrangement of claim 7 wherein said electrode is formed with a roll until use with said electrical pin connector.

10. The arrangement of claim 7 wherein said electrically conductive layer has a series of spaced pairs of apertures therein substantially aligned with said series of spaced pairs of apertures in said non-conductive layer so that said electrical pin connector when inserted through said apertures in said non-conductive layer also passes through said substantially aligned apertures in said electrically conductive layer, and wherein said electrode includes an electrically non-conductive protective strip positioned between said electrically conductive layer and said electrically conductive adhesive layer with said protective strip being adjacent to said series of pairs of spaced apertures in said electrically conductive layer.

11. A longitudinally elongated electrode capable of being longitudinally sized, said electrode comprising:
   an electrically conductive layer;
   an electrically conductive adhesive layer contiguous to one side of said conductive layer; and
   an electrically non-conductive layer contiguous to the side of said conductive layer opposite to that of said adhesive layer, said non-conductive layer having a series of aperture means extending longitudinally along said electrode with each of said aperture means being capable of receiving electrical lead means for establishing an electrical connection through said aperture means to said electrically conductive layer, and said electrode being longitudinally sizable by severing a portion thereof containing at least one of said series of aperture means.

12. The electrode of claim 11 wherein said electrode is formed as an elongated strip.

13. The electrode of claim 12 wherein said elongated strip is formed into a roll.

14. The electrode of claim 11 wherein said electrically conductive layer has a series of aperture means therein substantially aligned with said series of aperture means in said non-conductive layer so that said electrical lead means when inserted through said apertures in said non-conductive layer also passes through said substantially aligned apertures in said electrically conductive layer, and wherein said electrode includes an electrically non-conductive protective strip positioned to extend along said conductive layer adjacent to said series of aperture means.

15. A method for forming a diagnostic electrode, said method comprising:

providing an electrical strip that includes at least an electrically conductive layer, an electrically conductive adhesive layer at one side of said conductive layer, and an electrically non-conductive layer at the other side of said conductive layer;

providing a series of spaced aperture pairs in said non-conductive layer with the apertures of each said pair being closely spaced with respect to one another;

severing a section of said electrical strip so that said severed section includes at least one of said aperture pairs;

inserting a connector pin having an end and a side inwardly of said end through one of said apertures of said aperture pair in said severed section and moving the pin through said aperture a distance sufficient to enable said end of said connector pin to extend from the electrode through the other aperture of said aperture pair whereby, when so positioned, said side of said connector pin is maintained in electrical engagement with said conductive layer.

16. The method of claim 15 wherein said electrical strip is formed into a roll, and said strip is unrolled as necessary from the roll to provide a section, when severed, of desired length.

* * * * *